United States Patent [19]

Ashton et al.

[11] Patent Number: 5,773,019

[45] Date of Patent: Jun. 30, 1998

[54] IMPLANTABLE CONTROLLED RELEASE DEVICE TO DELIVER DRUGS DIRECTLY TO AN INTERNAL PORTION OF THE BODY

[75] Inventors: Paul Ashton, Boston, Mass.; Paul A. Pearson, Lexington, Ky.

[73] Assignee: The University of Kentucky Research Foundation, Lexington, Ky.

[21] Appl. No.: 534,854

[22] Filed: Sep. 27, 1995

[51] Int. Cl.$^6$ .............................. A61F 2/02; A61F 2/14; A61K 47/30; A61K 9/22

[52] U.S. Cl. ...................... 424/423; 424/427; 514/772.2; 514/772.3; 604/890.1; 604/892.1; 623/6

[58] Field of Search ...................................... 424/423, 427; 604/890.1, 892.1; 514/772.2, 772.3; 623/6

[56] References Cited

U.S. PATENT DOCUMENTS

| | | |
|---|---|---|
| 3,416,530 | 12/1968 | Ness . |
| 3,832,252 | 8/1974 | Higuchi et al. . |
| 3,845,201 | 10/1974 | Haddad et al. . |
| 3,870,791 | 3/1975 | Haddad et al. . |
| 4,300,557 | 11/1981 | Refojo et al. . |
| 4,309,776 | 1/1982 | Berguer . |
| 4,309,996 | 1/1982 | Theeuwes . |
| 4,649,047 | 3/1987 | Kaswan . |
| 4,808,353 | 2/1989 | Nambu et al. . |
| 4,923,699 | 5/1990 | Kaufman . |
| 4,942,035 | 7/1990 | Churchill et al. . |
| 4,973,304 | 11/1990 | Graham et al. . |
| 5,091,185 | 2/1992 | Castillo et al. . |
| 5,128,144 | 7/1992 | Korsatko-Wabnegg et al. . |
| 5,137,728 | 8/1992 | Bawa . |
| 5,156,851 | 10/1992 | Castillo et al. . |
| 5,164,188 | 11/1992 | Wong . |
| 5,178,635 | 1/1993 | Gwon et al. . |
| 5,229,128 | 7/1993 | Haddad et al. . |
| 5,232,708 | 8/1993 | Castillo et al. . |
| 5,342,620 | 8/1994 | Chowhan . |
| 5,378,475 | 1/1995 | Smith et al. . |

OTHER PUBLICATIONS

Pearson, P.A., et al.; "Sustained Delivery and Clearance of Intraocular Cyclosporine"; *Investigative Opthalmology and Visual Science*, vol. 34, Issue No. 7, (1993); Abstract No. 3917–31.

Baker, C.W., et al.; "In Vitro And In Vivo Evaluation of Intravitreal Sustained Release Dexamethasone Devices"; *Investigative Opthalmology and Visual Science*, vol. 34, Issue No. 7, (1993); Abstract N0. 3919–33.

Guo, H., et al.; "Sustained Device for Coadministration of Suramin and Amiloride"; *Investigative Ophthalmology and Visual Science*, vol. 36, No. 4, Mar. 15, 1995; Abstract No. 779–687.

Cordahi, G.J., et al.; "Toxicity of Sustained Release Cyclosporin A in Non–Human Primate Eyes", *Investigative Ophthalmology and Visual Science*, vol. 36, No. 4, Mar. 15, 1995; Abstract No. 2509–476.

Cheng, C.K., et al.; "Intravitreal Sustained Release Dexamethasone Device in the Treatment of Experimental Uveitis", *Investigative Opthalmology and Visual Science*, vol. 35, No. 4, Abstract No.3370–4:00.

Enyedi, L.B., et al.; Pharmacokinetics and Toxicity of an Intravitreal Device Providing Sustained Release of Cyclosporine(CsA) and Dexamethasone(dex); *Investigative Opthalmology and Visual Science*, vol. 35, No. 4, Abstract No. 3015–8:30.

(List continued on next page.)

*Primary Examiner*—Carlos Azpuru
*Attorney, Agent, or Firm*—Lowe, Price, LeBlanc & Becker

[57] ABSTRACT

A simple and implantable sustained release drug delivery device with an inner core containing an effective amount of a low solubility agent covered by a non-bioerodible polymer coating layer that is permeable to the low solubility agent is disclosed. A method for treating a mammal to obtain a desired local or systemic physiological or pharmacological effect by surgically implanting such a sustained release drug delivery device into a mammal in need of treatment is also disclosed.

22 Claims, 15 Drawing Sheets

OTHER PUBLICATIONS

Bierly, J.R., et al.; "Inhibition of Corneal Neovascularization with Subconjunctival Sustained Release Trihydroxysteroid Implants"; *Investigative Opthalmology and Visual Science*, vol. 35, No. 4, Abstract No. 444–55.

Hainsworth, D.P., et al.; "Intravitreal Ciprofloxacin Via a Bioerodible Sustained Release Device"; *Investigative Opthalmology and Visual Science*, vol. 35, No. 4, Abstract No. 3421–7:15.

Pearson, P.A., et al.; "Sustained Delivery of Cyclosporine(CsA) and Dexamethasone(dex) in the Treatment of Experimental Proliferative Vitreoretinopathy", *Investigative Opthalmology and Visual Science*, vol. 35, No. 4, Abstract No. 3085–12:00.

Cheng, C., et al.; "Intravitreal Sustained–Release Dexamethasone Device in the Treatment of Experimental Uveitis"; *Investigative Opthalmology and Visual Science*, vol. 36, No. 2, Feb. 1995.

PERMEABLE POLYMER
DRUG CORE
SUPPORT RING

SUTURE

GLOBE SURFACE

IMPLANTABLE CONTROLLED RELEASE DEVICE TO DELIVER DRUGS DIRECTLY TO AN INTERNAL PORTION OF THE BODY

TECHNICAL FIELD

The present invention relates to a simple and implantable sustained release drug delivery device with an inner core containing an effective amount of a low solubility agent covered by a non-bioerodible polymer coating layer that is permeable to the low solubility agent. Also, the polymer coating layer holds the drug in the correct anatomic position and essentially prevents disintegration of the drug core while not significantly impairing the drug release rate. A method for treating a mammal to obtain a desired local or systemic physiological or pharmacological effect by surgically implanting the device into a mammal in need of treatment is also disclosed.

BACKGROUND

Uveitis is a disease of the eye which can be located throughout the eye including the posterior and anterior chambers of the eye as well as the vitreous body. Uveitis, the inflammation of the uvea, is responsible for about 10% of the visual impairment in the United States.

Panuveitis refers to inflammation of the entire uveal (vascular) layer of the eye. Posterior uveitis generally refers to chorioretinitis and anterior uveitis refers to iridocyclitis. The inflammatory products, that is, cells, fibrin, excess protein, of these inflammations are commonly found in the fluid spaces of the eye including the anterior chamber, posterior chamber and vitreous space as well as the tissue involved in the inflammatory response. Uveitis may occur following surgical or traumatic injury to the eye, as a component of an autoimmune disorder such as rheumatoid arthritis, Behcet's disease, ankylosing spondylitis, sarcoidosis, as an isolated immune mediated ocular disorder, i.e., pars planitis, iridodyclitis etc., unassociated with known etiologies, and following certain systemic diseases which cause antibody-antigen complexes to be deposited in uveal tissues. Together these disorders represent non-infectious uveitities.

Cyclosporine A, a 1.2 kd cyclic peptide which is essentially insoluble in water effectively inhibits the development of experimentally induced uveitis. In human trials, cyclosporine A has been shown to be effective in treating chronic uveitis, especially that associated with Behcet's disease.

Unfortunately, systemic therapy with cyclosporine A has serious drawbacks. Cyclosporine A used systemically has also been associated with a high incidence of renal toxicity, some cases of hepatotoxicity, hypertension, and an increased incidence of opportunistic infections. The systemic side effects of cyclosporine A are so severe and so common that its use to treat life-threatening or in some cases severe sight-threatening disease is not recommended. The systemic toxicity is such that the National Eye Institute has recommended that, for uveitis inflicting one eye, cyclosporine should not be administered. Finally, a systemic application of cyclosporine A is limited by its prohibitive cost. Also, it should be noted that because of poor ocular availability, topical delivery does not result in the obtention of therapeutic levels of the drug in the back of the eye.

Accordingly, there exists a strong need for the elimination of the undesirable physiological and economic problems associated with cyclosporine A treatment of uveitis, while maintaining the advantageous therapeutic properties of this treatment.

The systemic toxicity of cyclosporine A may be minimized by delivering the drug locally. Although direct intravitreal injection prevents experimental autoimmune uveitis (EAU), repeated injection is not a practical mode of administration.

Due to the risks that certain drugs impose, researchers have developed systems for administering such drugs to aid in the treatment of ailments and diseases. The systems have been designed largely to reduce and to control the release rate of incorporated drugs. However, these systems fail to achieve the surprising and unexpected results obtained by the present invention.

For example, U.S. Pat. No. 5,091,185 to Castillo et al. relates to implantable pellets for veterinary use comprising a bioactive material such as somatotropin coated with a polyvinyl alcohol polymer to prolong the release of the bioactive material after implantation. Parenteral administration of the coated pellet is by subcutaneous implantation and may be accomplished surgically or by injecting small pellets through a needle. However, the Castillo patent does not teach that the polyvinyl alcohol polymer should be heated to temperatures greater than about 100° C. to induce changes in the crystal structure of the polymer to render it non-erodible. Somatotropins are heat sensitive and rapidly decompose on heating above 100° C. so such heating would be impractical for the systems described in the Castillo patent.

U.S. Pat. No. 4,300,557 to Refojo et al. relates to an improved process for dispensing a lipid-soluble, labile drug by diffusion from an implantable silicon capsule to a site within an animal body being treated with the drug, wherein the silicon capsule is provided with a tube sealed at its distal end and through the interior wall of which is cut a longitudinal slit of 1 to 1.5 mm for filling the capsule following implantation. The capsule is surgically implanted near the site being treated so that the tube is accessible for filling without further surgical procedures. In another aspect of the invention, a drug is dispensed at a constant rate through an expandable, silicon microballoon implanted periocularly to an intraocular site within an animal body.

U.S. Pat. No. 4,649,047 to Kaswan relates to a method for the treatment of, for example, uveitis occurring throughout the globe of the eye, by topical administration of cyclosporine to the eye.

U.S. Pat. No. 4,923,699 to Kaufman discloses an eye treatment system wherein three dimensional particles of bioerodible material of a specific size which are suspended in a liquid carrier or ointment carrier having a pH acceptable to the eye are delivered topically to the eye. Various agents may be added to increase viscosity, promote suspension and/or improve ocular compatibility.

U.S. Pat. No. 3,832,252 to Higuchi et al. relates to a drug delivery device comprising an inner solid matrix with solid particles of drug dispersed therethrough. Any solid material chemically compatible with the drug and permeable to passage of the drug by diffusion can be employed.

U.S. Pat. No. 4,309,996 to Theeuwes relates to a system comprising a microporous diffuser for delivering a beneficial agent to a fluid environment of use at a zero order rate for an increased length of time at that rate. The system consists essentially of a microporous wall, or a part microporous part semi-permeable wall, surrounding a compartment having a space containing the agent separated by a partition from a space containing an expandable entity.

U.S. Pat. No. 4,309,776 to Berguer relates to an intravascular implantation device having a chamber for containing transplanted cells that is implanted in a wall of a blood vessel or to be implanted between an artery and a vein in a wall of each for the purpose of introducing hormonal components into the bloodstream of a human being. It is disclosed that the material of which the chamber-forming device is made must be tolerated in a blood vessel without causing thrombosis and should permit the choice of various degrees of porosity.

U.S. Pat. No. 4,973,304 to Graham et al. relates to devices which have use in medical or veterinary application as implants or as inserts. The devices can be implanted surgically into the body or introduced into a body cavity of a human patient or an animal such that the active substance diffuses out of the device through hydrogel windows into the surrounding body region. The device may be in the form of a tube of water-permeable material having at least one port in the tube wall.

The above described systems and devices are intended to provide sustained release of drugs effective in treating patients at a desired local or systemic level for obtaining certain physiological or pharmacological effects. However, there are many disadvantages associated with their use. The need for a better release system is especially significant in the treatment of uveitis. Thus, there remains a long-felt need in the art for an improved device for providing sustained release of a drug to a patient to obtain a desired local or systemic physiological or pharmacological effect.

DISCLOSURE OF THE INVENTION

Therefore, it is an object of this invention to provide a device suitable for the controlled and sustained release of a composition effective in obtaining a desired local or systemic physiological or pharmacological effect and which, once implanted, gives a continuous release to an affected area without requiring additional invasions into the region. Moreover, the present invention is designed to hold the low solubility agent in the correct anatomic location and to prevent disintegration of the inner core. By maintaining surface area, the present invention reduces fluctuations in release characteristics. In one embodiment, fluctuations caused by changes in the composition of the bathing fluid are also eliminated.

In one embodiment, the device includes an inner core comprising an effective amount of a low solubility agent, and a non-erodible polymer coating layer, the polymer layer being permeable to the low solubility agent, wherein the polymer coating layer partially or completely covers the inner core.

Another object of the present invention is to provide a method for treating a mammal, e.g., a human, to obtain a desired local or systemic physiological or pharmacological effect. The method includes securing the sustained release drug delivery device at an area where release of the agent is desired and allowing the agent to pass through the polymer coating layer to the desired area of treatment.

A further object of the invention is to provide an ocular device suitable for direct implantation into the eye. Such devices of the present invention are surprisingly found to provide sustained release controlled release of various compositions to treat the eye without risk of detrimental side effects.

An additional object of the present invention is to provide an ocular delivery system that could be applied to an intraocular lens to prevent inflammation or posterior capsular opacification.

Another object of the present invention is to provide a means of achieving and maintaining therapeutic levels of trans retinoic acid, cis retinoic acid and other related retinoid compounds in the eye.

The above and other objects of the invention will become readily apparent to those of skill in the relevant art from the following detailed description and figures, wherein only the preferred embodiments of the invention are shown and described, simply by way of illustration of the best mode of carrying out the invention. As is readily recognized the invention is capable of modifications within the skill of the relevant art without departing from the spirit and scope of the invention.

DESCRIPTION OF THE INVENTION

Figure 1:
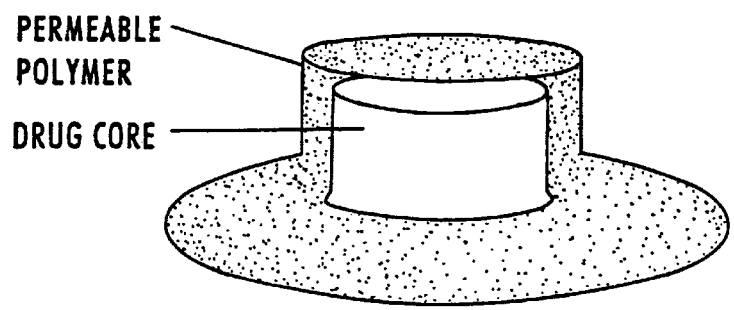
FIG. 1 is an enlarged view of an embodiment of the sustained release drug delivery device showing inner drug core and permeable polymer coating.
Figure 1:
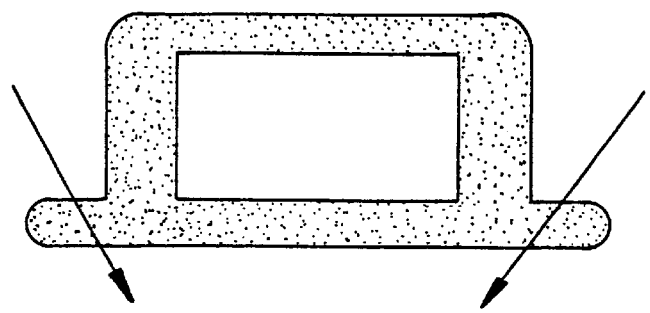
Figure 1:
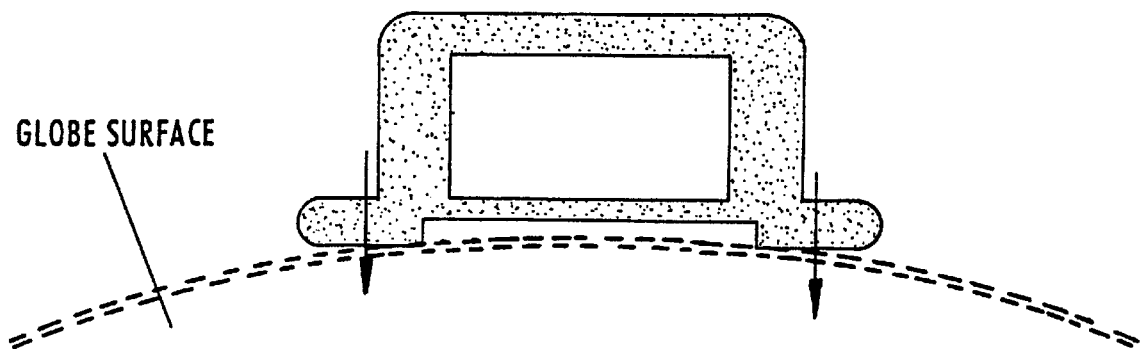

The present inventors have surprisingly and unexpectedly discovered a device that is suitable for the controlled and sustained release of an agent effective in obtaining a desired local or systemic physiological or pharmacological effect.

The device includes an inner core comprising an effective amount of a low solubility agent, and a non-bioerodible polymer coating layer, the polymer layer permeable to the low solubility agent, wherein the polymer coating layer covers the inner core.

Once implanted, the device gives a continuous supply of the agent to internal regions of the body without requiring additional invasive penetrations into these regions. Instead, the device remains in the body and serves as a continuous source of the agent to the affected area. In another embodiment, the device further comprises a means for attachment, such as an extension of the non-erodible polymer coating layer, a backing member, or a support ring. In a preferred embodiment, the device is suitable for direct implantation into the vitreous of the eye.

The device according to the present invention permits prolonged constant release of low solubility agents over a specific period of months (e.g., 3 months, 6 months) or years (e.g., 1 year, 5 years, 10 years, 20 years) until the agent is substantially used up.

Suitable low solubility agents useful in the present invention include immune response modifiers such as cyclosporine A and FK 506, corticosteroids such as dexamethasone and triamcinolone acetonide, angiostatic steroids such as trihydroxy steroid, anti-parasitic agents such as atovaquone, anti-glaucoma agents such as ethacrynic acid, antibiotics including ciprofloxacin, differentiation modulators such as retinoids (e.g., trans-retinoic acid, cis-retinoic acid and analogues), anti-viral agents including high molecular weight low (10-mers) low solubility anti-sense compounds, anti-cancer agents such as BCNU, nonsteroidal anti-inflammatory agents such as indomethacin and flurbiprofen, codrugs including low solubility codrugs of salts or conjugates of synergistic pharmacological agents such as suramin/amiloride or 5-FU/THS, and combinations thereof. The compounds that may be employed in the practice of the present invention should be in low solubility form. Reference may be made to any standard pharmaceutical textbook for the procedures to obtain a low solubility form of a drug.

Material that may be suitable for fabricating the polymer coating layer of the device include naturally occurring or synthetic materials that are biologically compatible with bodily fluids and eye tissues, and essentially insoluble in bodily fluids with which the material will come in contact. In addition, the suitable materials essentially prevent interaction between the low solubility agent in the inner core of the device and proteinaceous components in the bodily fluid. The use of rapidly dissolving materials or materials highly soluble in eye fluids or which permit interaction between the low solubility agent in the inner core and proteinaceous components in the bodily fluids are to be avoided since dissolution of the wall or interaction with the proteinaceous components would affect the constancy of drug release, as well as the capability of the device to remain in place for a prolonged period. Suitable polymers useful in the present invention include polyvinyl alcohol, ethylene vinyl acetate, silicone, polylactic acid, nylon, polypropylene, polycarbonate, cellulose, cellulose acetate, polyglycolic acid, polylactic glycolic acid, cellulose esters or polyether sulfone. The polymer coating layer is non-bioerodible and is permeable to the low solubility agent without being release rate limiting.

The cyclosporines which are useful in the practice of the present invention may be both natural or synthetic cyclosporines. For example, cyclosporine A may be used in the practice of the present invention. Other forms of cyclosporines (e.g., isomers) may also be used. Mixtures of at least two different cyclosporines may be used. The only requirement is that the cyclosporine possess the required activity vis-a-vis uveitis and is of extremely low solubility.

This device enables a large variety of drugs and other agents to be delivered into any internal region of the body, preferably the eye. Cyclosporine A in low solubility form is a preferred drug used in the delivery device.

The non-bioerodible polymer coating layer of the present invention may completely or partially cover the inner core. In this regard, any portion of the surface area of the inner core up to and including 100% may be coated with the polymer coating layer as long as the pellet is protected against disintegration, prevented from being physically displaced from its required site, and as long as the polymer coating layer does not adversely retard the release rate.

The method for treating a mammal to obtain a desired local or systemic physiological or pharmacological effect includes surgically implanting the sustained release drug delivery device of the present invention into the mammal and allowing agent to pass through the device to come in direct contact with the mammal.

The drug delivery device of the present invention may be administered to a mammal via any route of administration known in the art. Such routes of administration include intraocular, intraarticular, subcutaneous, vaginal, intramuscular, intraperitoneal, intranasal, dermal, and the like. In addition, one or more of the devices may be administered at one time or more than one agent may be included in the inner core.

The drug delivery device of the present invention is particularly suitable for direct surgical implantation into the eye.

The entire structure is made of material which is compatible with the human tissue with which it comes in contact. In a preferred embodiment the material of the device is polyvinyl alcohol. If a backing member is present in a preferred embodiment, the backing member may be composed of any material tolerated by the human body, preferably ethylene vinyl acetate, Teflon, silicone, silastic and nylon.

These methods of administration and technique for their preparation are well known by those of ordinary skill in the art. Techniques for their preparation are set forth in Remington's Pharmaceutical Sciences.

The drug delivery device may be administered for a sufficient period of time and under conditions to allow treatment of the disease state of concern.

For localized drug delivery, the device may be surgically implanted at or near the site of action. This is the case for devices of the present invention used in treating ocular conditions, primary tumors, rheumatic and arthritic conditions, and chronic pain. The device may be used to control the rate of drug delivery to any internal region of the body.

For systemic relief, the devices may be implanted subcutaneously, intramuscularly or intraperitoneally. This is the case when devices are to give sustained systemic levels.

The following examples are merely illustrative of the present invention and they should not be considered as limiting the scope of the invention in any way, as these examples and other equivalents will become more apparent to those skilled in the art in light of the present disclosure.

EXAMPLE 1

Figure 4:
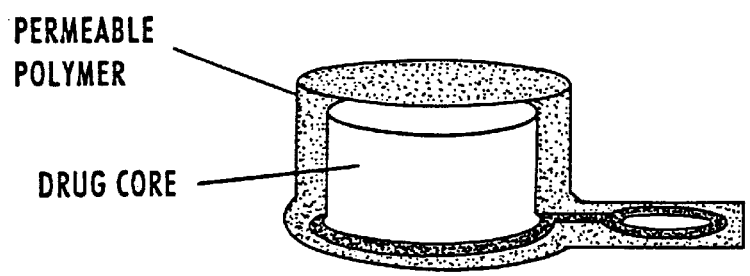
FIG. 4 is an enlarged view of an embodiment of the sustained release drug delivery device showing inner drug core, permeable polymer coating layer and an extension of the polymer coating layer containing a support ring as a means for attachment wherein the support ring forms a loop through which a suture can be passed.
Figure 4:
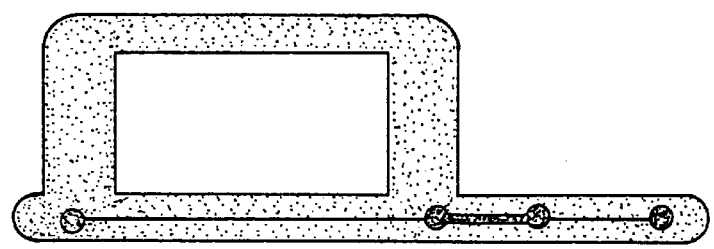
Figure 4:
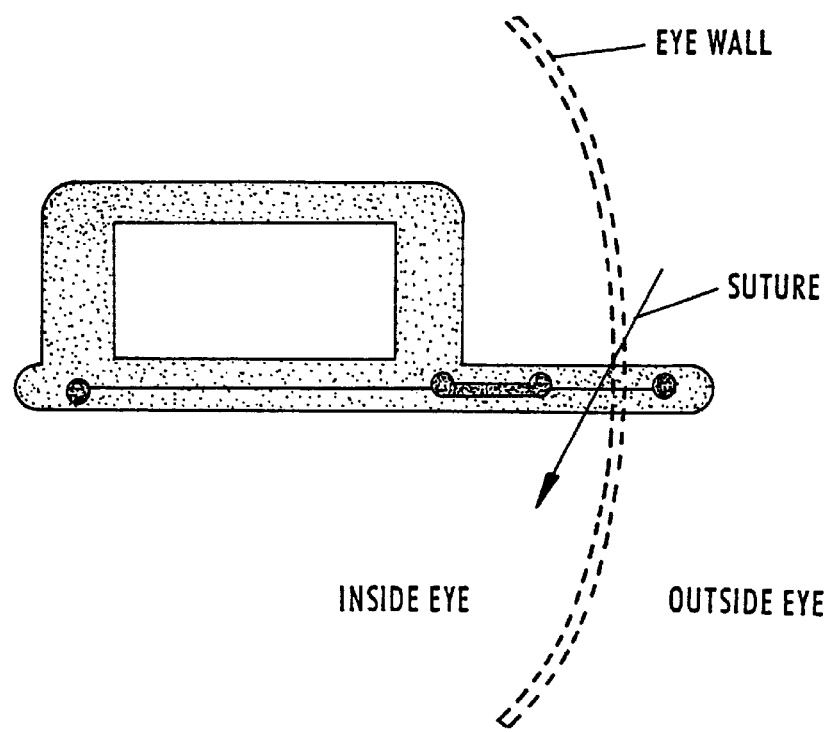
Figure 5:
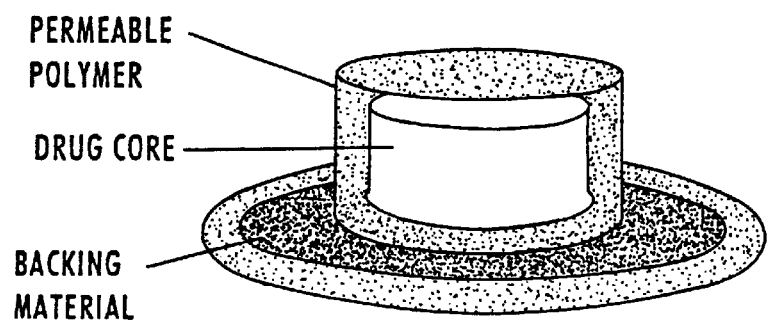
FIG. 5 is an enlarged view of an embodiment of the sustained release drug delivery device showing inner drug core, permeable polymer coating layer and an extension of the polymer coating layer containing a backing material as a means for attachment.
Figure 5:
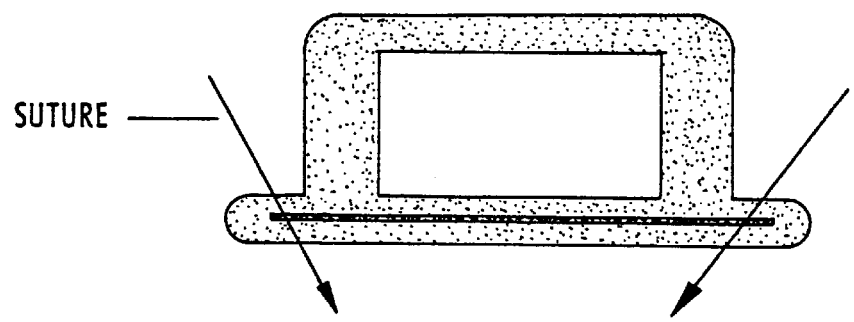
Figure 5:
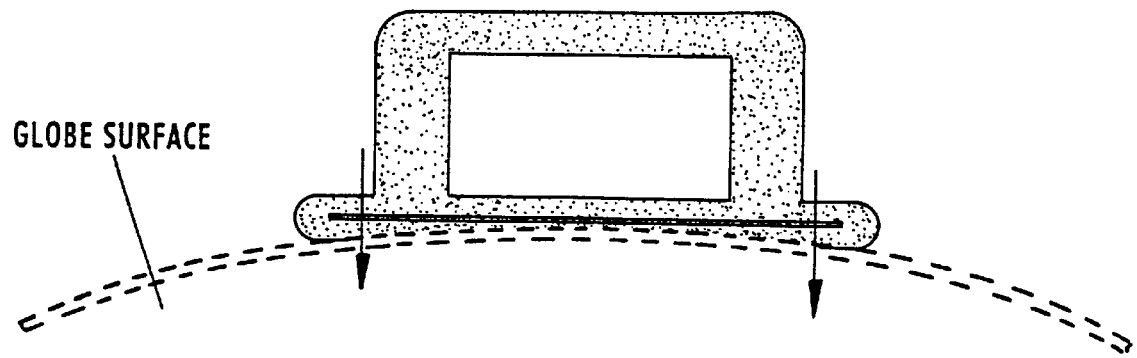
Figure 6:
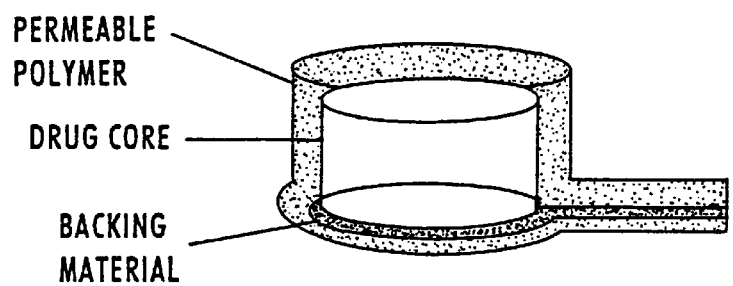
FIG. 6 is an enlarged view of an embodiment of the sustained release drug delivery device showing inner drug core, permeable polymer coating layer and an extension of the polymer coating layer containing a backing material as a means for attachment.
Figure 6:
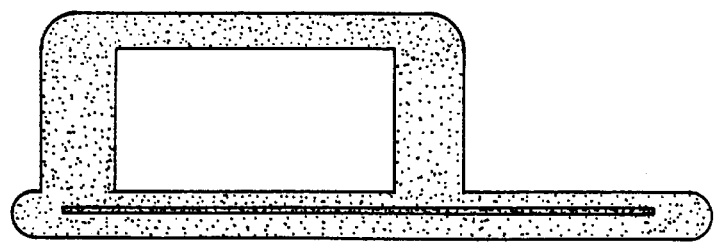
Figure 6:
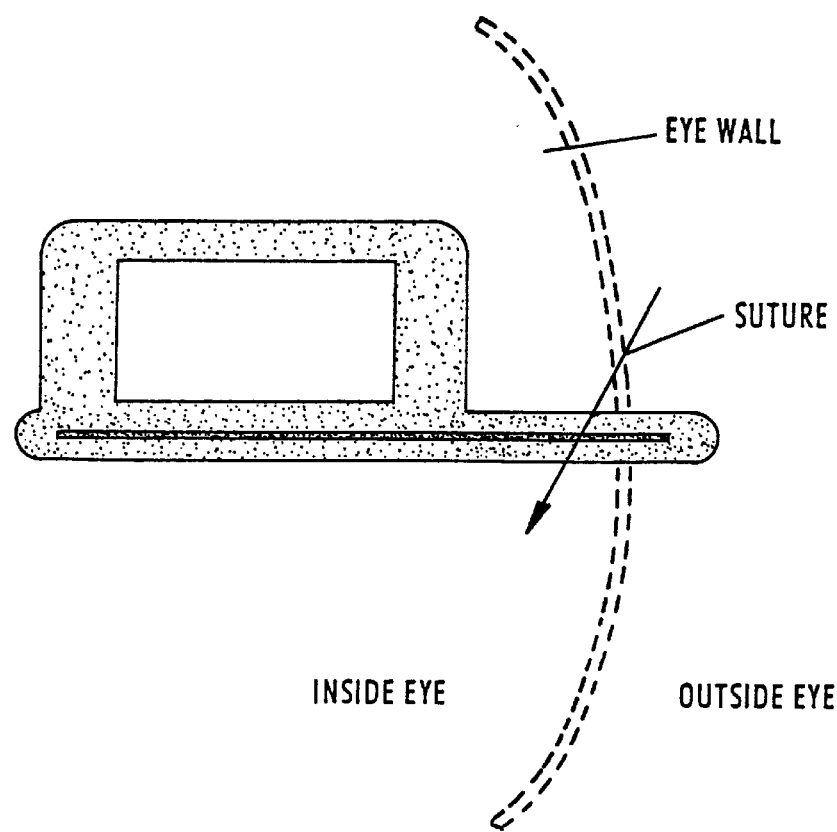

A device according to the present invention was prepared. This device was composed of a 5 mg core of cyclosporine A (obtained from the National Eye Institute as a gift) coated in polyvinyl alcohol (PVA) (obtained from Polysciences, Inc.) and heated at 110° C. for 10 minutes. In design it resembled FIG. 2. The device was implanted into the vitreous of 3 monkeys and appeared safe. Another monkey received an identical pellet and after 6 months was sacrificed and a sample of vitreous obtained. Analysis showed the concentration of cyclosporine to be 60 ng/ml. This indicates that the system can be used to maintain therapeutic levels of drug (in this case cyclosporine) in the eye for prolonged periods. Due to the "soft" nature of PVA when heated to 110° C. an improved device would contain a support ring or backing (FIGS. 4 or 6).

EXAMPLE 2

Figure 3:
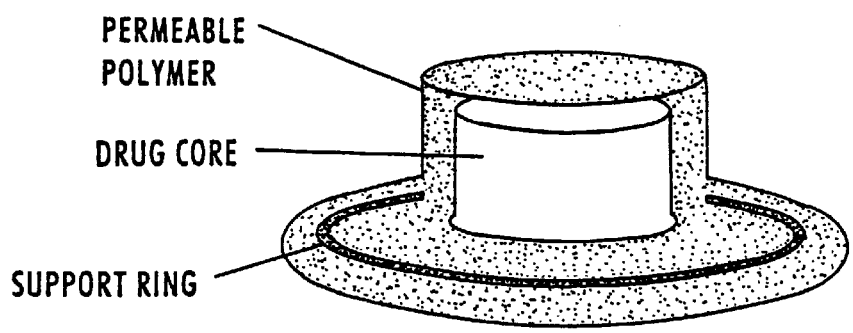
FIG. 3 is an enlarged view of an embodiment of the sustained release drug delivery device showing inner drug core, permeable polymer coating layer and an extension of the polymer coating layer containing a support ring as a means for attachment wherein the support ring allows enough space for a suture to be passed between the drug core and the support ring.
Figure 3:
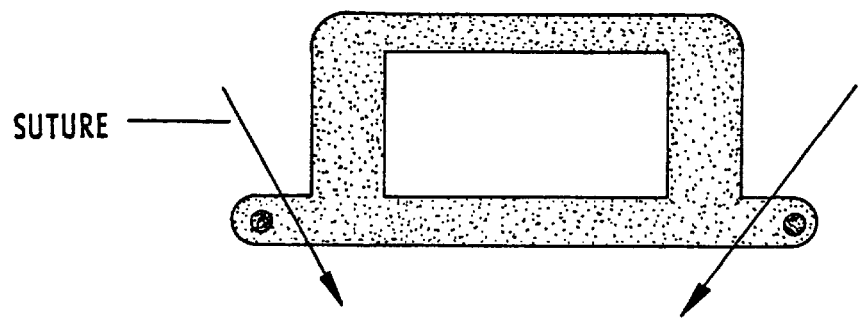
Figure 3:
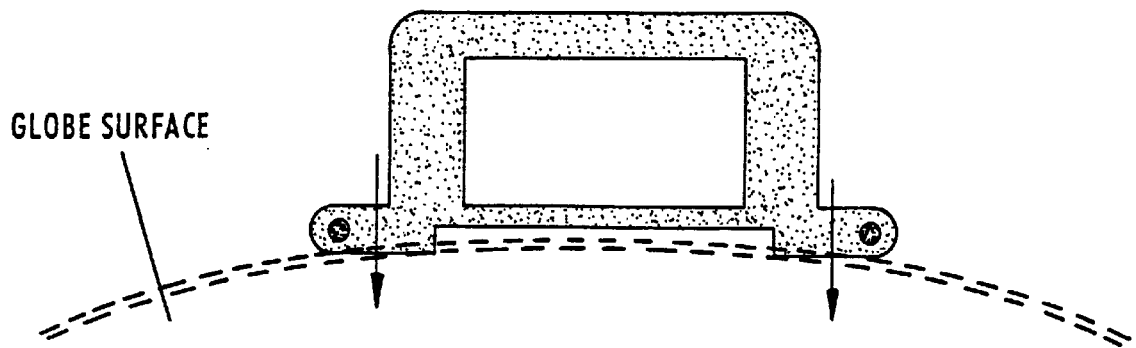

A device according to the present invention was prepared. This device was composed of a 3 mm, 12 mg disc of retinoic acid encased in silicone. It resembles FIG. 3 in appearance. The implant was prepared by preparing a thin film of silicone. A 2.5 mm hole was then cut through the film and the retinoic acid pellet fixed directly over the hole using silicone. A loop of Prolene suture was placed over the pellet and fixed onto the surface of the film so that a "gap" of over 1 mm was present between the pellet and the suture all the way around. The entire assembly was then coated again in silicone. These pellets were sutured onto the surface of the sclera in 3 rabbits and the ERGs taken every week for 5 weeks. There was no evidence of toxicity.

EXAMPLE 3

Figure 2:
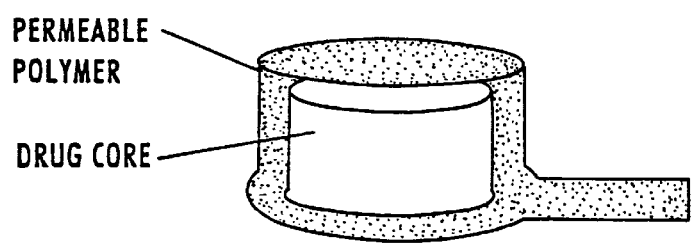
FIG. 2 is an enlarged view of an embodiment of the sustained release drug delivery device showing inner drug core, permeable polymer coating of the present invention and an extension of the polymer coating layer as a means for attachment.
Figure 2:
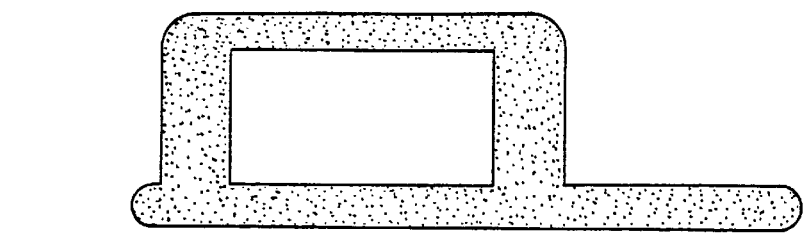
Figure 2:
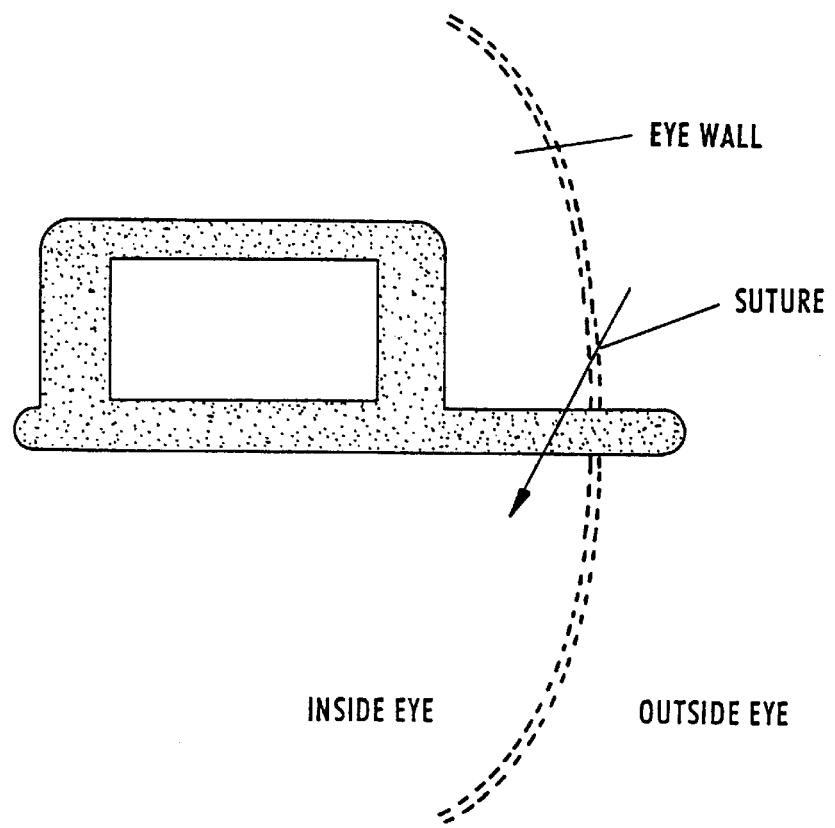

Pellets of retinoic acid were prepared by compressing 2 mg of the compound in a 1.5 mm Parr Instruments Press. Some pellets were then coated in PVA and heated to 120° C. and trimmed leaving a suture tab attached as shown in FIG. 2 while other pellets were not coated. Uncoated pellets and devices were immersed in 1 ml of phosphate buffer (pH 7.4) containing 0.5% albumin at 37° C. After 24 hours the buffer was replaced with fresh and the amount of drug released calculated by HPLC. After approximately 25 days buffer containing 1.0% albumin was added and the experiment continued.

Figure 7:
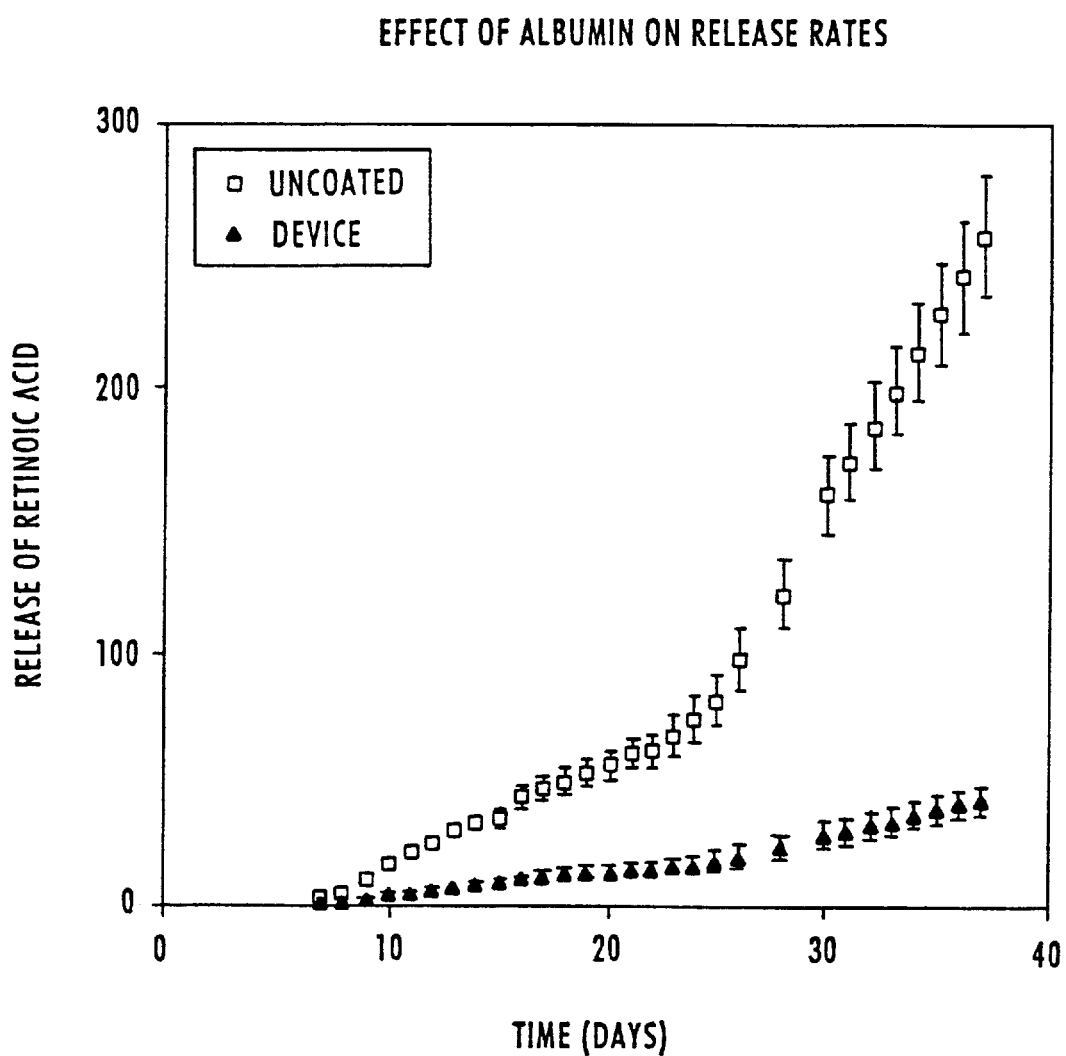
FIG. 7 shows a graph indicating that 0.5% albumin uncoated retinoic acid pellets release significantly faster than retinoic acid in the devices according to the invention.

As can be seen from the graph depicted in FIG. 7, in 0.5% albumin uncoated retinoic acid pellets release significantly faster than retinoic acid in the devices. This is due in part to the coating preventing small particles of powder from flaking from the surface and increasing the surface area. Increasing the albumin concentration greatly increases the release rate of retinoic acid from the pellets but has minimal effect on release from the device.

This stabilization is important in many diseases, especially ophthalmic diseases. In some eye diseases the albumin concentration of the vitreous and aqueous can increase by a factor of 40. Without the release stabilizing properties of the device this would cause a huge increase in release rate with unforetold consequences.

EXAMPLE 4

All animal procedures were performed using New Zealand albino rabbits of either sex weighing approximately 2 kg and adhered to the guidelines set forth by the Association for Research in Vision and Ophthalmology for animal use in research.

Twenty four animals (Group 1) were used. Cyclosporine was mixed into stock solutions of 50:50 ethanol:water at a concentration of 1 $\mu$g/20 $\mu$l and 10 $\mu$g/20 $\mu$l. $^3$H-labeled cyclosporine (1 $\mu$Ci/20 $\mu$l) was also added to the stock solution. Animals were anesthetized with ketamine (60 mg) and xylazine (20 mg) and the pupils were dilated with one drop of phenylephrine hydrochloride (2.5%) and tropicamide (1%). An intravitreal injection of cyclosporine was then given through the superior rectus muscle approximately 5 mm posterior to the limbus using a 30 gauge needle. Twelve animals received a dose of 1 $\mu$g(20 $\mu$l) and 12 animals received a dose of 10 $\mu$g(20 $\mu$l). The injection was given into the midvitreous cavity and care was taken to avoid the lens. For the 1 $\mu$g group, 3 animals were sacrificed at 0.5, 3, 6 and 24 hours. For the 10 $\mu$g group, 3 animals were sacrificed at 0.5, 6, 24 and 48 hours. The eyes were enucleated and then immediately frozen at $-70°$ C. Tissues were prepared for assay as described below. Intravitreal half-life and volume of distribution were determined from regression analysis of a 1 n concentration versus time plot.

Figure 8:
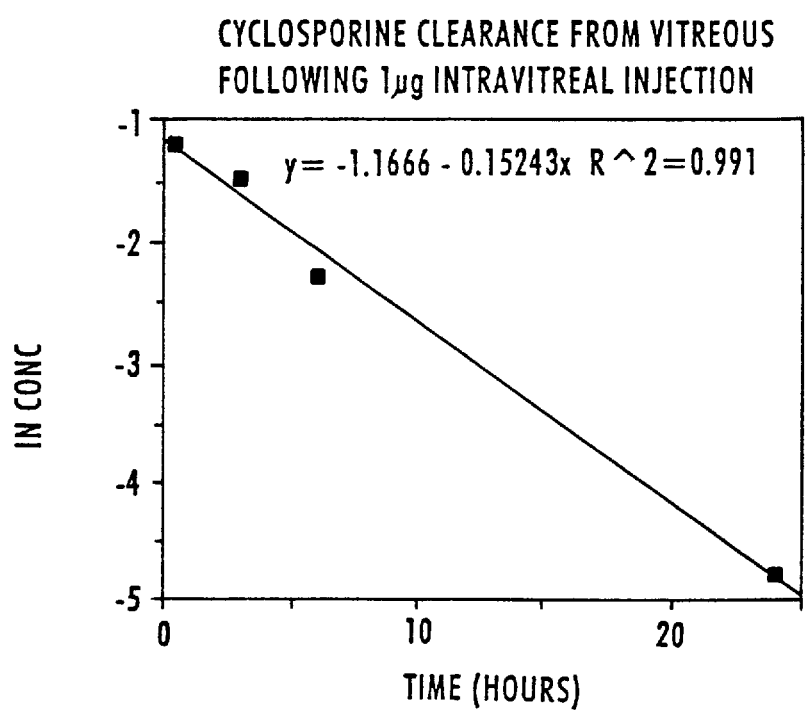
FIG. 8 shows clearance of cyclosporine from the vitreous following a 1 µg injection.
Figure 9:
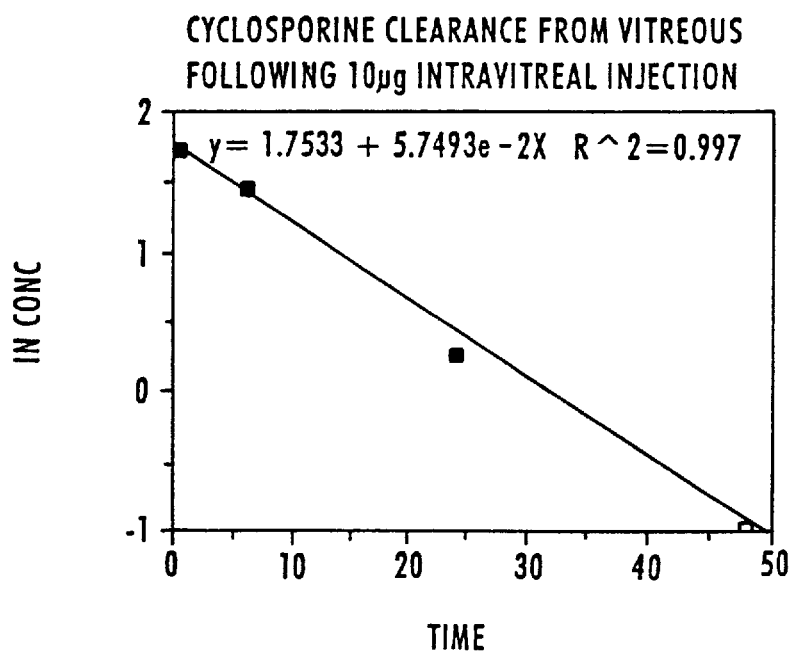
FIG. 9 shows clearance of cyclosporine from the vitreous following a 10 µg injection.
Figure 10:
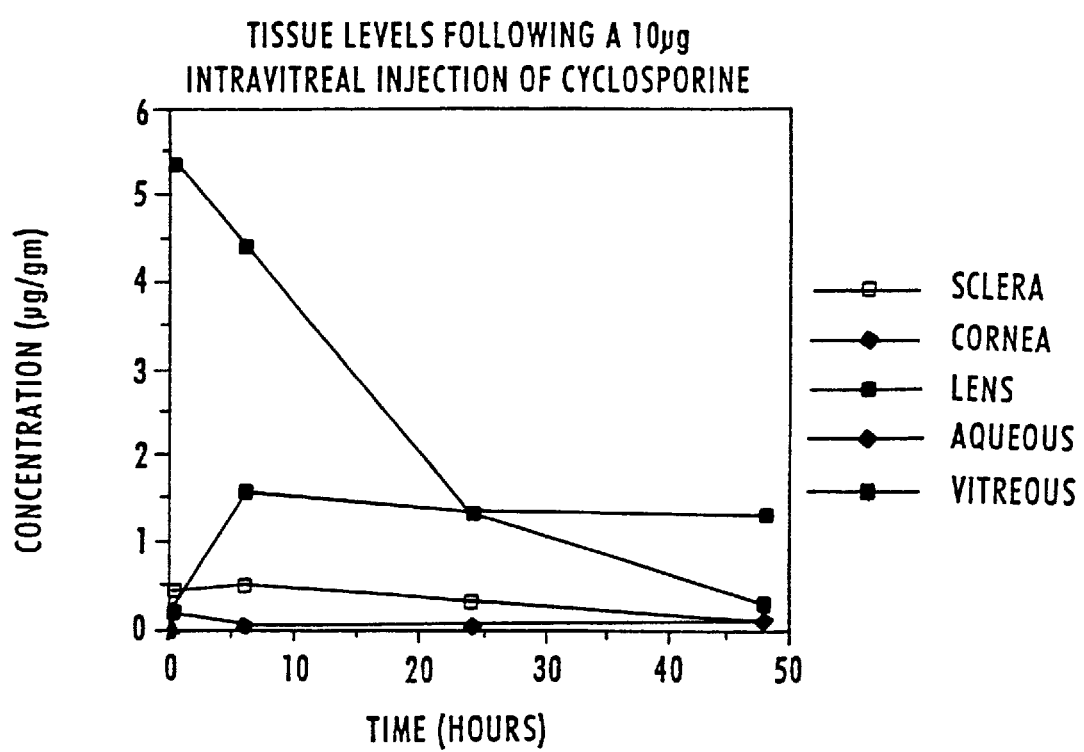
FIG. 10 shows tissue levels of cyclosporine following a 10 µg injection into the midvitreous.

Following a 1 $\mu$g injection the regression equation of 1 n concentration versus time for vitreous levels was y=1.17–0.15x ($R^2$=0.99) which equates to a half-life of 4.2 hours and distribution volume of 3.2 ml (FIG. 8). Following the 10 $\mu$g injection the regression equation for vitreous levels was y=1.75–0.058x ($R^2$=0.99) which equates to a half-life of 10.8 hours and a volume of distribution of 1.7 ml (FIG. 9). Analysis of tissue samples (FIG. 10) demonstrated relatively high lens levels. The drug content in the lens remained high throughout the study period. Thirty minutes following the 1 $\mu$g injection the amount of cyclosporine in the vitreous was 0.39 $\mu$g while the total drug present in all of the remaining ocular tissue samples was 0.27 $\mu$g. Thus the ratio of total tissue cyclosporine to vitreous cyclosporine was 0.69. Thirty minutes after the 10 $\mu$g injection there was 7 $\mu$g of cyclosporine in the vitreous and 0.75 $\mu$g of cyclosporine in the tissues which equates to a total tissue cyclosporine to vitreous cyclosporine ratio of 0.11.

EXAMPLE 5

Eighteen animals (Group 2) were used. Devices consisted of a core of 5 mg of cyclosporine which wa labeled with 13.6 $\mu$Ci $^3$H-cyclosporine.

The core, which measured 2.5 mm in diameter, was coated with several layers of polyvinyl alcohol and then heat treated at 104° C. for one hour. Under anesthesia, cryopexy was applied to the superior temporal quadrant. The cryopexy was placed 3 mm posterior and parallel to the limbus and extended 4 mm from the superior rectus muscle towards the lateral rectus. Two weeks later an incision was made through this area of cryopexy and the device was inserted into the vitreous and secured to the sclera. Animals were sacrificed at 1, 2, 4, 9, 18 and 26 weeks with an overdose of pentobarbital. The eyes were enucleated and immediately frozen at $-70°$ C. and then the tissues were prepared for assay as described below.

At the time of dissection, the devices were removed and placed in 15 ml of 95% ethanol to extract the drug remaining in each device. Samples of this solution were analyzed and the amount of residual drug was calculated for each device. Three devices were randomly chosen and analyzed in a similar fashion to determine the amount of drug in the device at time zero.

Eyes from Examples 4 and 5 were dissected while still frozen. Tissue samples (cornea, lens, iris, and retina/sclera) were separated and placed whole into 15 ml of scintillation fluid. The aqueous and vitreous were placed in separate glass vials and then 50 µl was removed and placed in 5 ml of scintillation fluid. To maximize drug recovery, the pipette tip was rinsed at least five times with scintillation fluid by drawing it up and expelling it back into the vial. One week later, the samples were analyzed using a Beckman LS7800 (Irvine, Calif.) scintillation counter. These data (disintegrations per minute) were then converted to drug concentration. Tissue samples were weighed prior to placement into the scintillation fluid and results expressed as µg cyclosporine per gm wet weight.

Extraction/counting efficiency for each tissue was determined by analysis of control tissues spiked with known concentrations of $^3$H cyclosporine. Tissues were immersed in scintillation fluid and periodically counted until equilibria were established. Using this technique the following extraction/counting efficiencies were obtained: cornea= 53±7%, lens=31±4%, sclera/retina=34±5% (mean±SD). Recovery from control vials containing no tissue was 100±3%. Percentage recovery was used to convert the measured concentration to corrected concentration for all tissue samples. This analysis was not performed for the iris because of difficulty in reliably adding the solution to the tissue without "contaminating" the vial.

Figure 11:
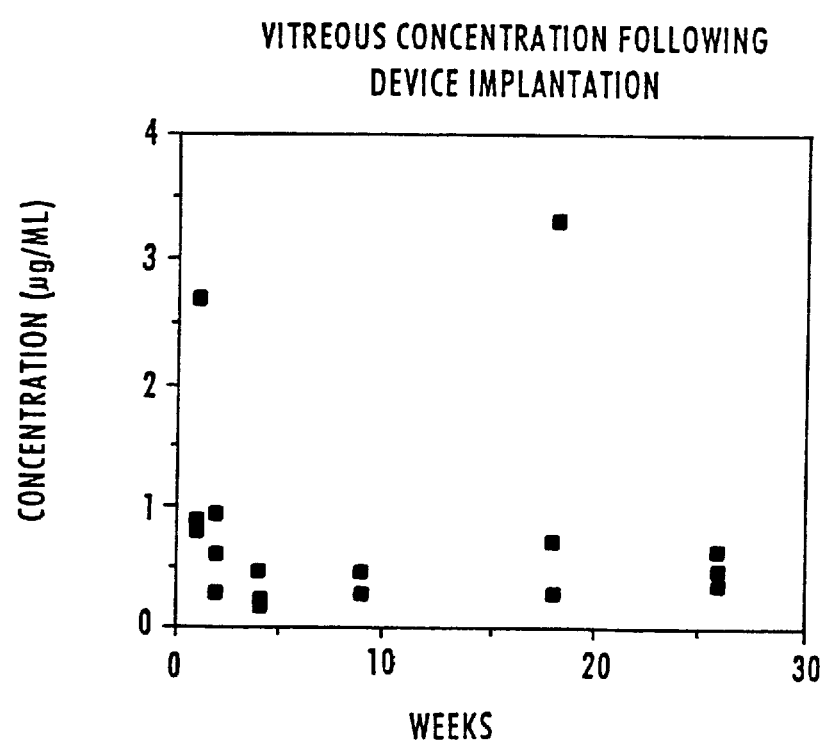
FIG. 11 shows vitreous concentration of cyclosporine following device implantation measured over 6 months.
Figure 12:
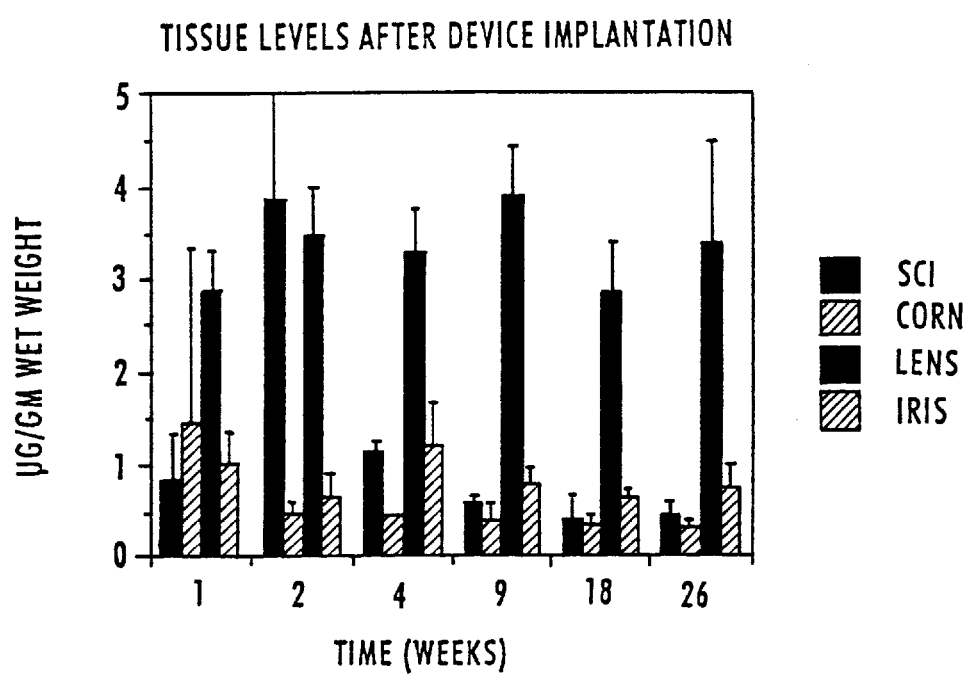
FIG. 12 shows tissue levels of cyclosporine following device implantation measured over 6 months. Note relatively high levels in the lens. Bars represent SEM.

The device produced steady and sustained ocular levels of cyclosporine. If all time points are included the average vitreous concentration was 0.76 µg/ml (range 0.18–3.3 µg/ml). In two eyes the measured vitreous concentration was significantly higher than this average (2.7 µg/ml and 3.3 µg/ml) and appeared to be the result of sampling error based on correlation with tissue concentrations in these eyes. With these two eyes excluded, the average vitreous concentration was 0.50 µg/ml. Vitreous levels are shown in FIG. 11. Tissue levels following device implantation (FIG. 12), similar to levels following intravitreal injection, were most significant for relatively high levels in the lens. Based on drug recovered from explanted devices there was no significant decrease in the amount of drug in the device at any time point when compared to devices assayed for drug content at time zero.

EXAMPLE 6

Eleven animals (Group 3) were used. Devices used were identical to those described in Example 5 except they contained non-radio labeled cyclosporine. Each animal underwent cryopexy in the temporal quadrant bilaterally as described above. Two weeks later a drug device was inserted into the right eye. A device consisting of polymers only was inserted into the left eye. Prior to device insertion an examination consisting of ophthalmoscopy and electroretinography (ERG) was performed. Scotopic and photopic electroretinograms (ERG's) were recorded from both eyes using contact lens electrodes (ERG-Jet) with a two-channel clinical signal averager (Cadwell 5200, Kennewick, Wash.) and a Ganzfeld flash unit (Cadwell VPA-10, Kennewick, Wash.). Dark adapted ERGs, performed after at least 30 minutes of dark adaptation, were elicited at 0.33 Hz and 20 stimulus presentations were averages. Light adapted ERGs were performed at 2.8 Hz after at least 5 minutes of light adaptation and were also the average of 20 stimuli. Resultant waves were evaluated for amplitude and latency. To minimize the effect of individual and daily variation (13–15) the ERG responses were evaluated using a ratio of the amplitude of the experimental (right) to the amplitude of the control (left). When the amplitudes of the experimental and control eyes are equal, the ratio equals 1. A decrease in the ratio reflects a relative decrease in the amplitude of the experimental eye.

Examinations were repeated on days 1, 7, 14 and then every two weeks for the next 6 months. Three animals were sacrificed at 6 weeks and two animals were sacrificed at 16 weeks. To assess for reversible toxicity the device was removed from 3 animals at 16 weeks. These animals were examined weekly for two months and then sacrificed. The remaining two animals were sacrificed at 26 weeks. Following sacrifice, the animals were perfused with fixative (either 10% buffered formalin or 6% phosphate buffered glutaraldehyde) via the left ventricle. The eyes were enucleated and placed in fixative. Three 3 mm by 6 mm specimens from the posterior pole were then embedded in either paraffin or plastic and sectioned. One section from each specimen was examined in a masked manner for evidence of toxicity.

Figure 13:
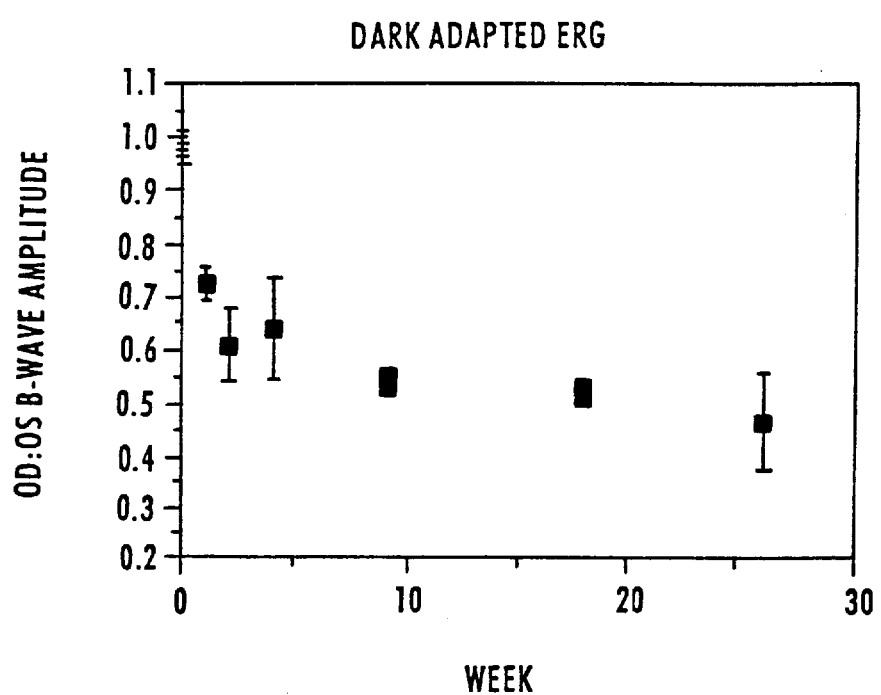
FIG. 13 shows ERG data demonstrating decrease in scotopic b-wave amplitude. Data represented as the ratio b-wave amplitude in drug eye to b-wave amplitude in control eye. Bars represent SEM.
Figure 14:
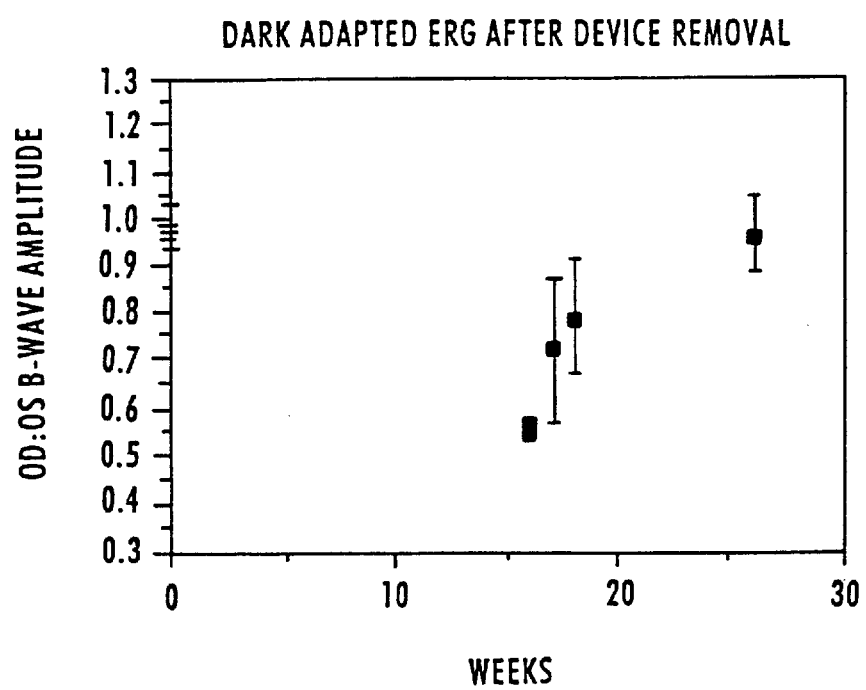
FIG. 14 shows ERG data demonstrating recovery of ERG following removal of the sustained release device containing cyclosporine. Data represented as the ratio b-wave amplitude in drug eye to b-wave amplitude in control eye. Bars represent SEM.

One animal died of an undetermined etiology immediately after device implantation. ERG examination of the remaining eyes demonstrated a decrease in the b-wave amplitude under both photopic and scotopic conditions in the drug containing eye at one week. This diminution of the b-wave progressed over the next month and then remained stable over the remainder of the study period (FIG. 13). The latency and amplitude of the scotopic a-wave were normal in all eyes. By one month a small focal posterior capsule opacification was present in the eyes containing drug. This cataract was located directly over the implant and did not progress. The remainder of the examination was normal. No control eyes developed either a decrease in the b-wave amplitude or the focal lens opacification noted in the drug treated eyes. In the three animals that had the device removed at week 16, the ERG returned to normal (FIG. 14). This change occurred by 2 weeks in two of the animals. In the third animal the ERG remained depressed and examination revealed a small white clump in the vitreous believed to be residual cyclosporine left in the eye due to device damage at the time of explanation. Over the next two months this clump gradually diminished in size and as it became smaller the ERG returned to near normal. The focal lens opacification in these three animals also gradually resolved and by the time of sacrifice, except for a small amount of vitreous haze at the implant site, the examination was normal in all 3 animals. Histopathologic examination revealed no difference in the drug and control eyes.

EXAMPLE 7

Three cynomologous monkeys were used. Animals were anesthetized using ketamine (30 mg/kg) for all procedures. Drug containing devices containing 6 mg of cyclosporine were implanted into the right eye and control devices consisting of polymer alone were implanted into the left eye as described. The monkey has a well developed pars plana so cryopexy was unnecessary. All devices were implanted 3 mm posterior to the limbus in the inferior temporal quadrant. Animals were anesthetized at 1 week, 2 weeks, 4 weeks, 2 months, 4 months, and 6 months and underwent examination with indirect ophthalmoscopy and electroretinography. Electroretinography was performed as described except that averages of 5 responses were acquired with a Nicolet CA-1000 clinical averager (Madison, Wis.) and a CKA Ganzfeld flash (Gaithersburg, Md.). At 6 months a sample of blood was analyzed by HPLC for cyclosporine (detection limit=25 ng/ml). After 6 months the animals were sacrificed with an overdose of pentobarbital and then were immediately perfused via the left ventricle with 10% buffered formalin. Eyes were placed in fixative and then subsequently embedded in paraffin, sectioned and examined in a masked fashion for evidence of toxicity.

While the levels of cyclosporine produced by the device of the present invention resulted in focal lens opacification and a decrease in the b-wave amplitude in the rabbit, there was no evidence of toxicity from the sustained intravitreal delivery of cyclosporine in the cynomologous monkey. The lens remained clear and there was no change in the ERG during the 6 month study period. Humans have a retinal anatomy similar to the primate and also have a larger vitreous volume which may serve to lower the steady state concentration of cyclosporine within the vitreous. Serum levels of cyclosporine were not detected in the monkey. This is consistent with the slow rate of drug release and systemic distribution of the drug and is further evidence that local, intraocular delivery would not be associated with systemic toxicity.

Figure 15:
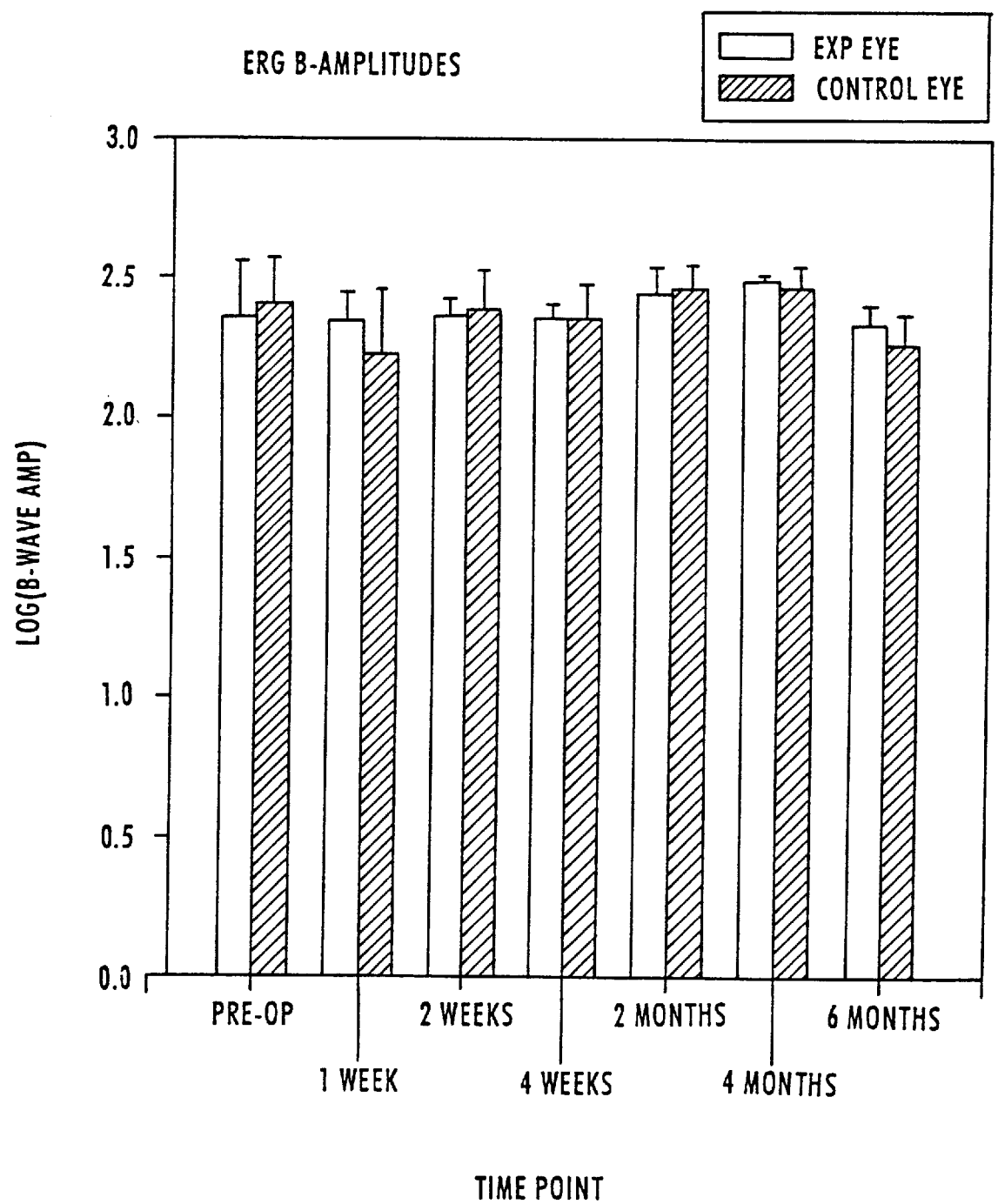
FIG. 15 shows ERG data in the monkey over 6 months demonstrates no evidence of retinal toxicity. Bars represent SEM.

There was no evidence of toxicity based on clinical examination, i.e., there was no evidence of cataract formation. The ocular media remained clear and the retina appeared normal throughout the study. The intraocular devices at 6 months had no visually apparent change in the amount of cyclosporine present in the device. There was no evidence of toxicity based on electroretinography. Specifically, the b-wave amplitude remained normal throughout the study (FIG. 15). Histopathologic analysis did not reveal any evidence of drug related toxicity. In one eye there was a small amount of inflammation noted around the intrascleral portion of the device. This inflammation appeared to surround both the suture and the polymer. Blood samples taken at 6 months did not have measurable levels of cyclosporine.

The clearance of cyclosporine following intravitreal injection was relatively rapid. This is consistent with the rapid clearance of other lipophilic compounds, such as steroids, which are able to exit the eye via a posterior route. The clearance of cyclosporine from the vitreous following the 1 µg injection was more rapid than following a 10 µg injection. There are several factors which may cause slower clearance of drug following administration of higher amounts of the drug: 1) The change observed may be artifactual resulting from drug loss during the sampling process. However, if this had occurred, the apparent elimination would not be expected to follow the first order kinetics observed as proportionally more cyclosporine would be lost at later time points; 2) Cyclosporine is a relatively insoluble compound and may precipitate at higher concentrations. If this occurred, elimination would not be expected to follow the first order kinetics observed; 3) Clearance may occur by a saturable active transport mechanism. Although this explanation would account for the decrease in elimination rate at higher concentrations, alone it would not cause the decrease in distribution volume noted (3.2 ml after 1 µg, 1.7 ml after 10 µg); 4) Partitioning into some tissue or layer may occur by a saturable mechanism. When this occurs by a saturable step, lower initial drug concentrations would be proportionally more affected resulting in a larger distribution volume. Partitioning appears to be the reason for the difference in elimination kinetics for the two doses. The ratio of total tissue cyclosporine to vitreous cyclosporine demonstrates that a much lower percentage of drug partitioned into the tissues following the 10 µg injection (from 0.69 to 0.11) which further supports a saturable partitioning effect as the mechanism of slower clearance of cyclosporine following the 10 µg injection. In the situation of sustained delivery, elimination mechanisms are likely to be saturated. Therefore, pharmacokinetic parameters determined following the 10 µg injection will apply.

The delivery device produced long-term sustained tissue and vitreous levels at a relatively low concentration. The release rate from the device can be estimated, based on parameters measured in the Examples. It is assumed that the release of drug from the device approximates a steady infusion in vivo based on prior experience with this type of device and on in vitro evaluation of this device. Under these conditions:

$$Css = IR/[Vd*(ln2)/T\tfrac{1}{2}]$$

where Css is concentration steady state, IR is the infusion (release) rate, Vd is the volume of distribution, and T½ represents the intravitreal half-life. The volume of distribution is 1.7 ml and the intravitreal half-life is 10.8 hours assuming these parameters can be approximated by the values derived from the 10 µg injection described above. The intravitreal steady state concentration produced by the device was approximately 0.6 µg/ml and thus the release rate of the device is approximately 1.3 µg/day. This rate indicated that the device would provide sustained intravitreal levels for about 10 years. The present inventors were unable to measure a significant decrease in the drug core of the device over 6 months. The variability in the quantity of cyclosporine incorporated in the drug core (5 mg±10%) at the time of construction combined with the relatively small decline in drug over the course of the study (decrease of 5% based on calculated release rate) diminished the ability to detect small changes in the drug core over time but the relatively constant drug levels in the core over the six month observation period demonstrates that the true release rate of the device is very slow.

EXAMPLE 8

Ciprofloxacin is normally supplied as the HCl salt. Free ciprofloxacin was prepared from a solution of the salt by neutralization with 1.0M NaOH and filtration of the precipitate. 2 mg of free ciprofloxacin was then compressed into 1.5 mm diameter by 1.0 mm pellets using a Parr Instruments customized pill press. A 5% solution of PLA was used as a "glue" to fix a 7-0 nylon suture to the pellet.

EXAMPLE 9

Release from these devices was determined at 37° C. by immersion in 1 ml of phosphate buffer (pH 7.4) or a solution composed of 20% serum: 80% phosphate buffer. The entire media was removed every 24 hours for 6 days and replaced with fresh, preheated media. Samples were again assayed by HPLC. Release from this device was linear over the duration of the study and was relatively independent of serum concentration. On a separate study, release was linear over a twenty day period.

EXAMPLE 10

Intravitreal ciprofloxacin levels were determined in New Zealand white rabbits (2–3 kg). Animals were divided into two groups and received either subconjunctival injection of a ciprofloxacin suspension or an intravitreal device. The drug reservoir type device was used in the animal studies as it was found to be most promising in vitro. All animals were treated according to institutional guidelines on the use of animals in research.

EXAMPLE 11

Ciprofloxacin suspensions for injection were prepared by weighing 5 mg of sterile ciprofloxacin directly into sterile syringes and adding 1 ml of sterile isotonic saline. Immediately before injection sealed syringes were sonicated for 60 minutes to ensure homogeneity.

The first group of animals received a subconjunctival injection of 5 mg of ciprofloxacin. Two animals were sacrificed after 1, 3 and 7 days and their eyes immediately enucleated and frozen at −70° C.

EXAMPLE 12

The remaining group of 8 animals received intravitreal implants in each eye. Animals were anesthetized with a 50:50 mixture of ketamine and rompun and topical proparacaine and eyes were then dilated with 1% mydriacyl and 2.%% phenylephrine. After a superior temporal conjunctival peritomy, an MVR blade was used to make a 2 mm scleral incision 2 mm posterior and parallel to the limbus. Devices were then inserted into the vitreous and visualized through the dilated pupil. The suture was passed through the incision and the device secured adjacent to the scleral wall. The same suture was then used to close the wound. The conjunctiva was closed and Polysporin ointment was placed in the eye. Flash and 20 Hz flicker electroretinograms (ERG) were performed immediately before implantation and sacrifice. Eyes were examined by slit lamp and indirect biomicroscopy immediately before sacrifice.

Animals were sacrificed after 1, 3, 7 and 14 days. Eyes were immediately enucleated and frozen at −70° C. Vitreous and aqueous analyses were performed as described above. 4 eyes were used for each time point. At the time of sacrifice, devices were removed from the vitreous, dissolved in an acetonitrile/water mixture, and assayed by HPLC to determine the amount of ciprofloxacin remaining in the device.

After subconjunctival injection of a ciprofloxacin suspension, particles of drug could be observed in the subconjunctival space for 7 days. Nevertheless, ciprofloxacin concentrations in both the aqueous and vitreous were below the assay quantitation limit at all time points (<0.2 ug/ml). In contrast, eyes receiving sustained release devices maintained vitreous levels of ciprofloxacin above 1 ug/ml (the $MIC_{90}$ for most pathogens).

Analysis of vitreous from eyes receiving the reservoir device showed mean vitreous level of 2.2 +/−0.8 ug/ml which was maintained throughout the duration of the study. Analysis of explanted devices showed that release was linear while in the vitreous with a mean release rate of 2.5 ug/hr and would correspond to a mean device duration of 4 weeks.

ERG examinations showed no significant difference in the pre- and post-implantation waveforms or amplitudes, despite the sustained drug level in the vitreous. Slit lamp examination showed mild vitreous cell at 7 days that had resolved by 14 days. Indirect biomicroscopy showed the devices to be stable with no migration and no retinal detachment.

The purpose of the above description and examples is to illustrate some embodiments of the present invention without implying any limitation. It will be apparent to those of skill in the art that various modifications and variations may be made to the device and method of the present invention without departing from the spirit or scope of the invention. All patents and publications cited herein are incorporated by reference in their entirety.

We claim:

1. A sustained release drug delivery device comprising:
    an inner core comprising an effective amount of a low solubility agent selected from the group consisting of immune response modifiers, corticosteroids, angiostatic steroids, anti-parasitic agents, anti-glaucoma agents, antibiotics, anti-sense compounds, differentiation modulators, anti-viral agents, anti-cancer agents, nonsteroidal anti-inflammatory agents, and low solubility codrugs; and
    a non-bioerodible polymer coating layer, the polymer layer being permeable to the low solubility agent, wherein the polymer coating layer covers the inner core and is essentially non-release rate limiting.

2. The device according to claim 1, wherein the polymer coating layer holds the inner core in correct anatomic position and essentially prevents disintegration of the low solubility agent.

3. The device according to claim 2, wherein the polymer coating layer essentially reduces interaction between the low solubility agent in the inner core and proteinaceous components in surrounding bathing fluid to prevent enhanced release.

4. The device according to claim 1, wherein the low solubility agent is selected from the group consisting of cyclosporine A, trans-retinoic acid, cis-retinoic acid, other retinoids, and low solubility anti-sense compounds.

5. The device according to claim 1, wherein the polymer comprises a heat-treated polyvinyl alcohol.

6. The device according to claim 1, wherein the polymer is silicone.

7. The device according to claim 1, further comprising a means for attachment.

8. The device according to claim 4, wherein the means for attachment is selected from the group consisting of an extension of the polymer coating layer, a backing member or a support ring.

9. The device according to claim 1, wherein the inner core consists essentially of an effective amount of a low solubility agent or a pharmaceutically acceptable salt.

10. The device according to claim 1, wherein the polymer coating layer completely covers the inner core.

11. The device according to claim 1, consisting essentially of:
    the inner core comprising an effective amount of the low solubility agent; and
    the non-bioerodible polymer coating layer, the polymer layer being permeable to the low solubility agent, wherein the polymer coating layer covers the inner core.

12. A method for treating a mammalian organism to obtain a desired local or systemic physiological or pharmacological effect comprising:
    surgically implanting a sustained release drug delivery device into a mammal in need of such treatment, the drug delivery device comprising:
    an inner core comprising an effective amount of a low solubility agent selected from the group consisting of immune response modifiers, corticosteroids, angiostatic steroids, anti-parasitic agents, anti-glaucoma agents, antibiotics, anti-sense compounds, differentiation modulators, anti-viral agents, anti-cancer agents, nonsteroidal anti-inflammatory agents, and low solubility codrugs; and a non-bioerodible polymer coating layer, the polymer layer being permeable to the low solubility agent, wherein the polymer coating layer covers the inner core and is essentially non-release rate limiting.

13. The device according to claim 12, wherein the polymer coating layer holds the inner core in correct anatomic position and essentially prevents disintegration of the low solubility agent.

14. The method according to claim 13, wherein the polymer coating layer essentially eliminates interaction between the low solubility agent in the inner core and proteinaceous components in surrounding bathing fluid to prevent enhanced release.

15. A method according to claim 12, wherein the device is surgically implanted within the eye.

16. A method according to claim 12, wherein the device is attached to an intraocular lens or a haptic extending from the intraocular lens.

17. A method according to claim 12, wherein the treatment is for uveitis, age related macular degeneration, and cytomegalovirus retinitis.

18. A method according to claim 12, wherein the polymer coating layer is essentially insoluble and inert in body fluids and compatible with eye tissues.

19. A method according to claim 12, wherein the agent is selected from the group consisting of cyclosporine A, trans-retinoic acid, cis-retinoic acid, other retinoids, and low solubility anti-sense compounds.

20. A method according to claim 12, wherein the sustained release device is surgically implanted at a desired location.

21. A method according to claim 12, wherein the sustained release device delivers an effective amount of the low solubility agent for at least 5 years.

22. A method according to claim 12, wherein the sustained release device delivers an effective amount of the low solubility agent for at least 10 years.

* * * * *